(12) United States Patent
Young et al.

(10) Patent No.: US 12,396,774 B2
(45) Date of Patent: Aug. 26, 2025

(54) ORTHOPAEDIC CEMENT REMOVAL TOOLS AND METHOD

(71) Applicant: RADLEY SCIENTIFIC LIMITED, Ashburton (GB)

(72) Inventors: Stephen Michael Radley Young, Newton Abbot (GB); Sean Martin Badcott, Paignton (GB)

(73) Assignee: RADLEY SCIENTIFIC LIMITED, Ashburton (GB)

( * ) Notice: Subject to any disclaimer, the term of this patent is extended or adjusted under 35 U.S.C. 154(b) by 1081 days.

(21) Appl. No.: 17/279,572

(22) PCT Filed: Sep. 25, 2019

(86) PCT No.: PCT/GB2019/000141
§ 371 (c)(1),
(2) Date: Mar. 24, 2021

(87) PCT Pub. No.: WO2020/065245
PCT Pub. Date: Apr. 2, 2020

(65) Prior Publication Data
US 2021/0338297 A1    Nov. 4, 2021

(30) Foreign Application Priority Data

Sep. 25, 2018 (GB) .................................... 1815640

(51) Int. Cl.
*A61B 17/32* (2006.01)
*A61B 17/88* (2006.01)
*A61N 7/00* (2006.01)

(52) U.S. Cl.
CPC ............ *A61B 17/8847* (2013.01); *A61N 7/00* (2013.01)

(58) Field of Classification Search
CPC .................... A61B 17/320068; A61B 17/8847
See application file for complete search history.

(56) References Cited

U.S. PATENT DOCUMENTS

| | | | | |
|---|---|---|---|---|
| 4,846,161 A | * | 7/1989 | Roger ................ | A61B 17/8847 606/82 |
| 5,151,099 A | * | 9/1992 | Young .................... | A61N 7/00 606/92 |

(Continued)

FOREIGN PATENT DOCUMENTS

| | | |
|---|---|---|
| GB | 2296457 | 7/1996 |
| WO | WO2017011263 | 1/2017 |

OTHER PUBLICATIONS

English translation of Office Action issued in Japanese Patent Application No. 2021-517033 dated Jun. 27, 2023, nine (9) pages.

(Continued)

*Primary Examiner* — Nicholas W Woodall
(74) *Attorney, Agent, or Firm* — Andrew D. Dorisio; Dickinson Wright PLLC

(57) ABSTRACT

A series of surgical tools (11, 21, 31, 41, 51, 61, 71, 81) have respective operative heads (16, 26, 36, 46, 56, 66, 76, 86 & 96) mounted adjacent a distal end of an elongate waveguide (12, 13, 14). The operative heads (16, 26, 36, 46, 56, 66, 76, 86 & 96) are used to remove PMMA bone cement (2, 5) from within a hollow bone (1), such as a femur (1), as part of a prosthesis revision operation, such as replacement of an artificial hip joint. Torsional-mode ultrasonic vibrations are transmitted along the waveguide (12, 13, 14) to the respective operative heads (16, 26, 36, 46, 56, 66, 76, 86 & 96), which are applied to the bone cement (2, 5), softening it and facilitating its removal. Elongate radial channels (18, 23, 28, 38) extend across cement-contacting faces of several of the surgical tools (11, 21, 31, 41, 71, 81), acting to focus and transmit the torsional-mode ultrasonic vibrations into adjacent cement (2, 5). In another tool (51), scalloped recesses (58, 59) in its cement-contact face have substantially the same effect, while in a further tool (61), a series of notches (65) along a distal edge (69) of the tool (61) have an (Continued)

analogous function. The operative heads (76, 86, 96) of certain tools (71, 81) can be embedded into a cement plug (5) then used to pull the plug (5) as a unit out of the bone (1).

20 Claims, 9 Drawing Sheets

(56) References Cited

U.S. PATENT DOCUMENTS

| | | | | |
|---|---|---|---|---|
| D341,202 S | * | 11/1993 | Hood | D24/146 |
| 5,536,266 A | * | 7/1996 | Young | A61B 17/8847 |
| | | | | 606/92 |
| 5,891,149 A | * | 4/1999 | Young | A61N 7/00 |
| | | | | 606/92 |
| D893,029 S | * | 8/2020 | Qun | D24/146 |
| 2006/0004396 A1 | | 1/2006 | Easley et al. | |
| 2008/0051693 A1 | * | 2/2008 | Babaev | A61B 17/320068 |
| | | | | 118/620 |
| 2008/0058585 A1 | | 3/2008 | Novak | |
| 2017/0143398 A1 | * | 5/2017 | Young | A61B 17/8847 |
| 2023/0293212 A1 | * | 9/2023 | Badcott | A61B 17/8847 |
| | | | | 606/92 |

OTHER PUBLICATIONS

English translation of Office Action issued in Chinese Application No. 201980075730.9 dated Mar. 14, 2024, ten (10) pages.
European Office Action issued in connection with European Application No. 19794184.2 dated Jan. 10, 2024, three (3) pages.
International Search Report dated Dec. 10, 2019 issued in International Application No. PCT/GB2019/000141, ive (5) pages.
Written Opinion of International Searching Authority dated Dec. 10, 2019 issued in International Application No. PCT/GB2019/000141, eight (8) pages.

* cited by examiner

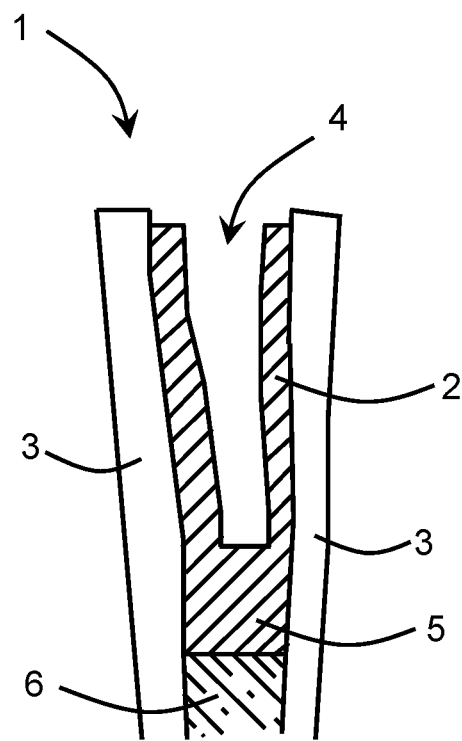
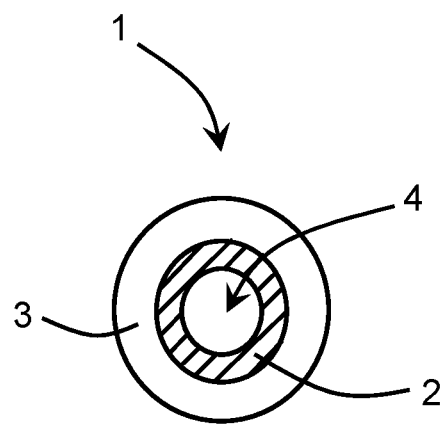
Fig 1A  Fig 1B
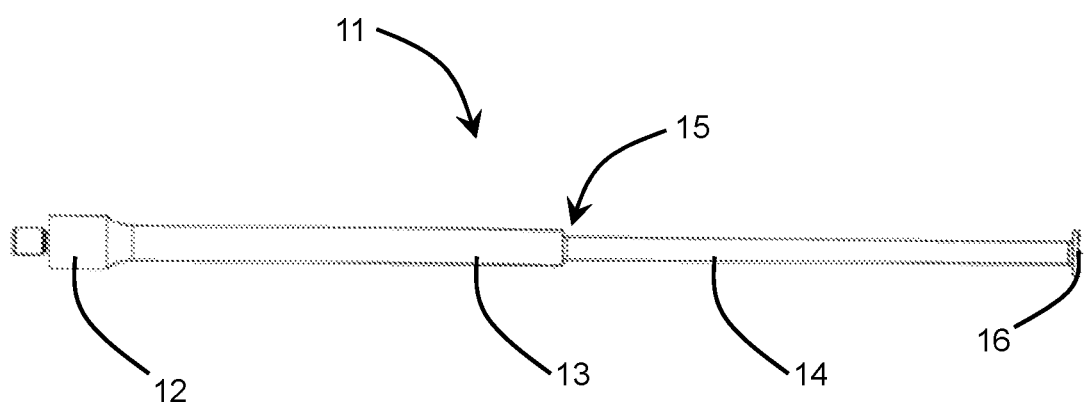
Fig 2

ORTHOPAEDIC CEMENT REMOVAL TOOLS AND METHOD

The present invention relates to surgical tools for removal of cement from bone cavities as part of a revision arthroplasty. More particularly but not exclusively, it relates to a set of ultrasonically-activatable tools for removal of PMMA cement following removal of a prosthesis from a bone cavity. The present invention further relates to a revision arthroplasty method using such tools.

Joint prostheses, such as hip joint implants, will comprise at least one component which is implanted into a hollow bone by means of a shaft inserted into a cavity of the bone. Some implants rely on growth of cancellous bone to anchor the shaft of the implant in the bone cavity, but poly(methylmethacrylate) cement (PMMA cement) is more commonly used, filling the space between the shaft of the implant and the inner walls of the bone cavity, and optionally also sealing the bone cavity distally to the distal end of the shaft.

Such implants have a limited lifetime, and so it is often necessary to revise a joint prosthesis by removing the old implant, cleaning the site and implanting a replacement prosthesis in its place (revision arthroplasty). The old cement must be removed or it may hinder adhesion of the new cement. The original approach for PMMA cement removal was simply chiselling it away which could take hours. A significant step forward came from the use of tools activated by longitudinal-mode ultrasonic vibrations, which caused localised softening of the cement, allowing for much easier removal. However, this method still has some drawbacks, for example associated with the difficulty of directing the effect of the longitudinal-mode vibrations solely where intended, and not, for example, cutting into adjacent structural bone. This is particularly important where the feature of the implant is due to weakening or damage to the adjacent bone, for example due to infection.

Torsional-mode ultrasonic vibrations have proved useful in cutting soft tissues, for example in laparoscopic (keyhole) surgery. However, the tools used in this application are not suitable for arthroplasty work.

It is hence an object of the present invention to provide tools for the removal of PMMA cement from bone cavities in the course of revision arthroplasty or the like, which obviate the above disadvantages and allow more rapid and accurate cement removal, particularly tools allowing effective application of torsional-mode ultrasonic vibrations to the cement. It is also an object of the present invention to provide a method of cement removal using such tools.

According to a first aspect of the present invention, there is provided a surgical tool for use in revision arthroplasty, adapted to be activated by torsional-mode ultrasonic vibrations, comprising elongate waveguide means adapted to transmit said ultrasonic vibrations to an operative head mounted adjacent a distal end of the waveguide means, wherein said operative head comprises a planar body extending transversely to a longitudinal axis of the waveguide means, and a distal face of said planar body comprises a plurality of concave recesses, each adapted to focus and project torsional-mode ultrasonic vibrations into material such as cement in contact with said distal face.

In a preferred embodiment, said planar body extends orthogonally to the longitudinal axis of the waveguide means.

It is also preferred that the planar body is mounted symmetrically to the distal end of the waveguide means.

It is further preferred that the planar body extends outwardly of the waveguide means to all sides.

Preferably, said concave recesses have an elongate form.

Advantageously, said elongate concave recesses radiate outwardly across the distal face of the planar body from a point in line with the longitudinal axis of the waveguide means.

The elongate concave recesses may advantageously be curved about their respective longitudinal axes.

The elongate concave recesses may thus adopt the form of fluting, channels, scallops or scoops radiating across the distal face of the planar body.

The distal face of the planar body may be provided with a distal projection located in line with the longitudinal axis of the waveguide means.

In a second embodiment of this aspect, a proximal face of the planar body also comprises a plurality of concave recesses, each adapted to focus and project torsional-mode ultrasonic vibrations into material such as cement in contact with said proximal face.

Preferably, said concave recesses are elongate.

Advantageously, the elongate concave recesses radiate outwardly across the proximal face of the planar body from its junction with the waveguide means.

The elongate concave recesses may continue from the proximal face of the planar body on to an outer surface of the waveguide means, so as to extend longitudinally along a distal portion of the waveguide means.

In this embodiment, the surgical tool may thus be used either with a distally-directed pushing motion into cement, or with a proximally-directed pulling motion, so as to scrape or scoop up cement.

In most embodiments of this aspect, the planar body is substantially circular.

The planar body may be provided with shallow notches or recesses around its circumference, optionally each aligned with an outer end of a respective elongate concave recess.

Thus, cement softened by the tool may more easily pass from a distal to a proximal side of the planar body.

In alternative embodiments of this aspect, the planar body is not circular, instead extending further outwardly in a first direction than in a second direction orthogonal to the first.

Optionally, the extent of the planar body in said second direction may correspond substantially to a diameter of the waveguide means.

A narrower end of the planar body may then be used to form narrow grooves in the cement, particularly in cement that is lining interior walls of a bone cavity.

In these embodiments, the tool may be further provided with a second planar body, extending transversely to the longitudinal axis of the waveguide means at a point proximal to the first planar body, said first and second planar bodies having substantially the same shape, size and alignment, but only the more distal of the planar bodies having recesses on its distal face.

According to a second aspect of the present invention, there is provided a surgical tool for use in revision arthroplasty, adapted to be activated by torsional-mode ultrasonic vibrations, comprising elongate waveguide means adapted to transmit said ultrasonic vibrations to an operative head mounted adjacent a distal end of the waveguide means, wherein said operative head comprises a planar body extending transversely to a longitudinal axis of the waveguide means, and a proximal face of said planar body comprises a plurality of concave recesses, each adapted to focus and project torsional-mode ultrasonic vibrations into material such as cement in contact with said proximal face.

In a preferred embodiment, said planar body extends orthogonally to the longitudinal axis of the waveguide means.

It is also preferred that the planar body is mounted symmetrically to the distal end of the waveguide means.

It is further preferred that the planar body extends outwardly of the waveguide means to all sides.

Preferably, said concave recesses on the proximal face of the planar body have an elongate form.

Advantageously, said elongate concave recesses radiate outwardly across the proximal face of the planar body from its junction with the waveguide means.

The elongate concave recesses may advantageously be curved about their respective longitudinal axes.

The elongate concave recesses may thus adopt the form of fluting, channels, scallops or scoops radiating across the proximal face of the planar body.

The elongate concave recesses may continue from the proximal face of the planar body on to an outer surface of the waveguide means, so as to extend longitudinally along a distal portion of the waveguide means.

In this aspect, the planar body of the operative head preferably has a flat distal face.

Thus, the surgical tool may be used with a proximally-directed pulling motion so as to scrape or scoop up cement.

According to a third aspect of the present invention, there is provided a surgical tool for use in revision arthroplasty, adapted to be activated by torsional-mode ultrasonic vibrations, comprising elongate waveguide means adapted to transmit said ultrasonic vibrations to an operative head comprising a distal tip of the waveguide means, said terminal extension wherein said operative head comprises a terminal extension of the waveguide means expanding frustoconically to a transversely-extending distal end face, said distal end face comprising a plurality of concave recesses, each adapted to focus and project torsional-mode ultrasonic vibrations into material such as cement in contact with said distal end face, and wherein the operative head comprises a plurality of slots extending radially inwardly from a circumference of the terminal extension and extending longitudinally from the distal end face through to a point on the waveguide means proximal to the terminal extension, said slots being adapted to allow passage of cement softened by the ultrasonically-vibrated operative head through the operative head.

Preferably, said radial slots have an overall surface area assessed at the distal end face that is equivalent to roughly half of the total area of the distal end face.

Advantageously, the radial slots become shallower towards their proximal ends.

The radial slots may divide the operative head into a plurality of lobes, connected by a central portion located on a longitudinal axis of the waveguide means and operative head.

There may be three radial slots dividing the operative head into three lobes.

According to a fourth aspect of the present invention, there is provided a surgical tool for use in revision arthroplasty, adapted to be activated by torsional-mode ultrtasonic vibrations, comprising elongate waveguide means adapted to transmit said ultrasonic vibrations to an operative head extending from a distal end of the waveguide means, wherein the operative head broadens out distally in a first lateral direction and tapers distally in a second lateral direction, towards its distal edge, said distal edge extending in a plane orthogonal to the longitudinal axis of the waveguide means and being curved within said orthogonal plane, in an arc displaced to one side of the longitudinal axis, a centre of curvature of said arc being located to an opposite side of the longitudinal axis from the arc.

The curvature of the arc is thus much shallower than the curvature of the circumference of the waveguide.

Preferably, said distal edge comprises a series of rounded notches extending proximally from the distal edge and defining a series of V-shaped teeth between them.

Said notches are advantageously adapted to focus and project torsional-mode ultrasonic vibrations distally from the distal edge of the operative head.

The operative head may comprise a first face extending generally in line with an adjacent portion of the waveguide means and a second face extending distally at an angle towards the first face to produce the distal taper.

Said second face of the operative head may have a slightly concave longitudinal profile.

According to a fifth aspect of the present invention, there is provided a method of removing cement from a bone cavity following removal of a implanted cemented prosthesis, comprising the steps of forming a plurality of longitudinal grooves onto the cement lining the walls of the bone cavity, using a first ultrasonically-vibratable surgical tool, each groove extending radially through the cement to the wall of the bone cavity, and then passing a second ultrasonically-vibratable tool in a distal direction between the cement and the wall of the bone cavity, so as to separate the cement in sections laterally demarcated by said grooves.

Preferably, the method further comprises the step of scraping any remaining cement off the walls of the bone cavity, using a third ultrasonically-vibratable surgical tool.

Advantageously, the first ultrasonically-vibratable surgical tool comprises a surgical tool as described in the alternative embodiment of the first aspect above, the second ultrasonically-vibratable surgical tool comprises a tool as described in the fourth aspect above, and the third ultrasonically-vibratable tool comprises a tool as described in either the second aspect or the second embodiment of the first aspect above.

According to a sixth aspect of the present invention, there is provided a method of removing a cement plug filling a bone cavity following the removal of an implanted cemented prosthesis, comprising the steps of driving a fourth ultrasonically-vibratable surgical tool, having an operative head comprising at least one rotationally non-symmetrical planar body, into the cement plug, while adjacent cement is still softened, twisting the operative head such that the at least one planar body passes laterally into the bulk cement, waiting until the cement has re-hardened and the tool is anchored into the cement, then manipulating the tool to exert force on the cement plug and extract it in one piece from the bone cavity.

Preferably, the fourth ultrasonically-vibratable surgical tool comprises a tool as described in the final embodiment of the first aspect above.

Embodiments of the present invention will now be particularly described by way of example and with reference to the Figures of the accompanying drawings, in which:

FIG. 1A is a scrap schematic longitudinal section of an upper part of a femur, from which a hip joint prosthesis has been removed;

FIG. 1B is a scrap schematic transverse section of the femur of FIG. 1A;

FIG. 2 is a side elevation of a first surgical tool embodying the present invention;

Figure 3A:
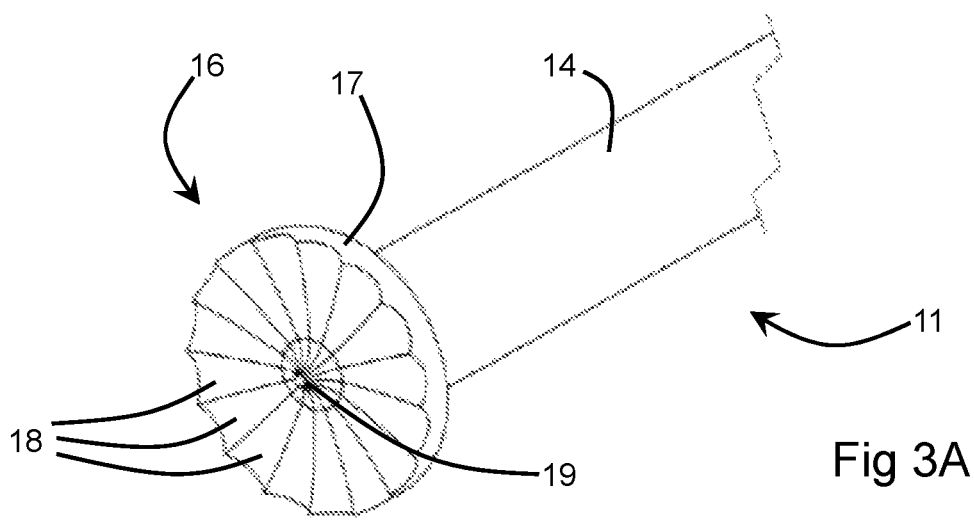
FIG. 3A is a scrap perspective view of an operative head of the surgical tool of FIG. 2.

Referring now to the Figures and to FIGS. 1A and 1B in particular, a proximal end portion of a human femur 1 is shown, which has previously been trimmed and a hip joint prosthesis implanted. This prosthesis has subsequently shown signs of impending failure, or has started to come loose from the femur 1, and so has been extracted by known methods, prior to implantation of a replacement prosthesis. Removal of the prosthesis has left a layer of PMMA cement 2 lining the walls 3 of the femur 1 and has left a void 4 where the prosthesis was, which allows convenient access to the layer of cement 2 (see below). In this example, a plug 5 of cement is located distally of the void 4, separating that portion of the bone cavity of the femur 1 that had been hollowed out to receive the prosthesis from a remainder of the bone cavity and bone marrow 6 therein. (In other procedures, more complex sealing devices are implanted in place of the simple cement plug 5, but these require different approaches for removal and revision, and will not be covered here).

FIGS. 1A and 1B will be referred to further below, in the context of the methods of use of the tools described herein. It should be noted that the proportions of the walls 3 of the femur 1, the cement layers 2 and the cement plug 5 shown here are chosen for clarity, and do not necessarily accurately represent the actual dimensions and proportions found in practice.

FIG. 2 is a side elevation of a first surgical tool 11 embodying the present invention. This comprises an elongate waveguide of titanium, with a connecting portion 12 at its proximal end for connection to a source of (torsional-mode) ultrasonic vibrations (not shown). In this example, the waveguide is made up of an elongate proximal section 13 and an elongate distal section 14, the proximal section 13 being of greater diameter. (Correct location of a step 15 in diameter between the proximal section 13 and distal 14 sections of the waveguide, to position it at a node in the vibrations, produces a significant amplification of the ultrasonic vibrations. A first operative head 16 is mounted to a distal tip of the distal section 14.

Figure 3B:
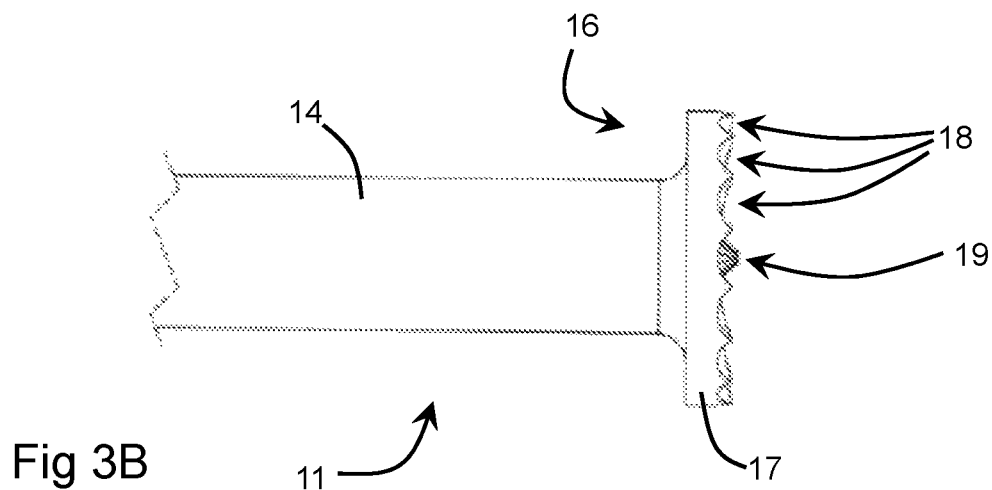
FIG. 3B is a scrap side elevation of the operative head of FIG. 3A.
Figure 3C:
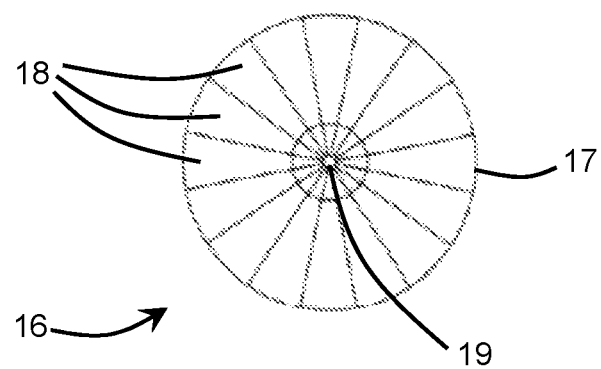
FIG. 3C is a distal end elevation of the operative head of FIG. 3A.

FIGS. 3A to 3C show the first operative head 16 in more detail. It comprises a discoidal body 17, mounted to a distal end of the distal section 14 of the waveguide, with the discoidal body 17 extending in a plane normal to the longitudinal axis of the waveguide, and with a centre of the discoidal body 17 located on said longitudinal axis. Sixteen identical round-bottomed channels 18 radiate outwardly across a distal face of the discoidal body 17, extending between a generally conical centrally-located prong or peak 19 and a circumference of the distal face. The prong/peak 19 extends slightly proud of a remainder of the distal face.

When the first surgical tool 11 is activated by the torsional-mode ultrasonic vibrations, the round-bottomed channels 18 focus the vibrations and project the energy into material in contact with or closely adjacent to the distal face of the first operative head 16. Since torsional-mode vibrations comprise a twisting motion back and forth about the longitudinal axis of the waveguide, the effect of this operative head 16 will be greater towards its periphery.

The first surgical tool 11 is used to soften PMMA bone cement ahead (distally) of the tool 11, allowing it to be pushed into the solid cement. Softened cement will flow around a periphery of the first operative head 16 from a distal face to a proximal face, and it may be possible to remove this material by retracting the first surgical tool (proximally) before it re-solidifies. This tool 11 can also be used to broaden a hole formed into solid cement by pushing it into cement adjacent the hole, with the distal face partly contacting the cement and partly overlapping the hole.

The first surgical tool 11 is thus mainly used in clearing out solid cement forming the cement plug 5, distal to the location 4 of the implant within the medullary cavity of the bone 1.

Figure 4A:
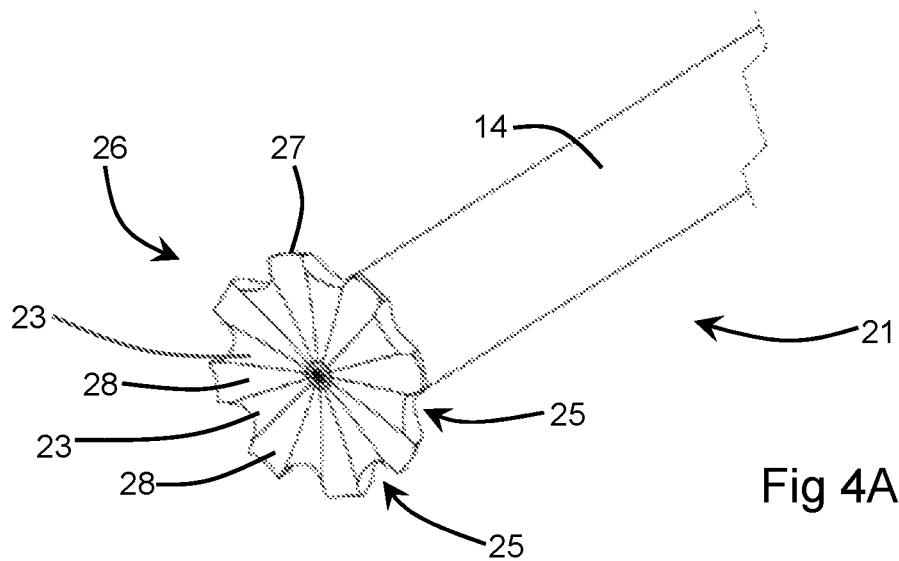
FIG. 4A is a scrap perspective view of an operative head of a second surgical tool embodying the present invention.
Figure 4B:
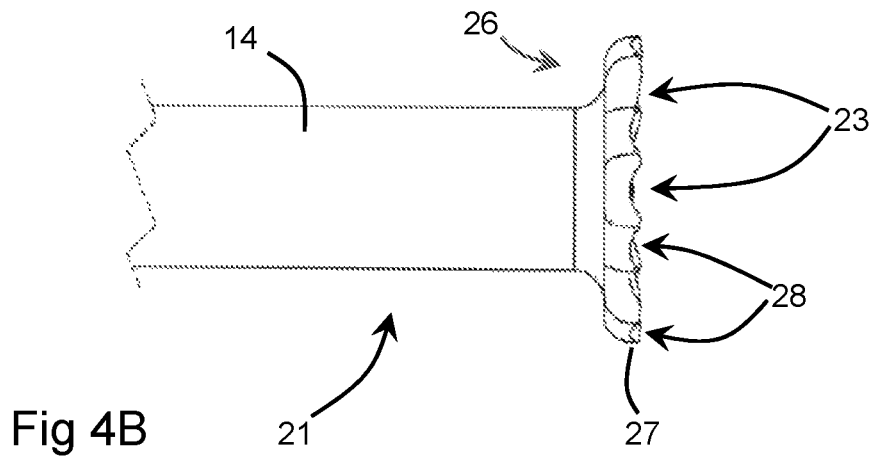
FIG. 4B is a scrap side elevation of the operative head of FIG. 4A.
Figure 4C:
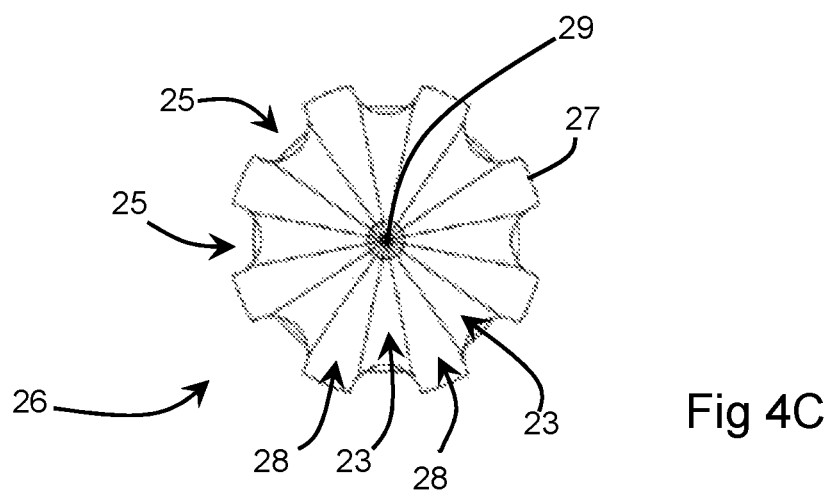
FIG. 4C is a distal end elevation of the operative head of FIG. 4A.

FIGS. 4A to 4C show a second operative head 26 of a second surgical tool 21. This also comprises a discoidal body 27, mounted to the distal end of the distal section 14 of the waveguide and extending at right angles to the longitudinal axis of the waveguide. The centre of the discoidal body 27 is again located on the longitudinal axis, and there is a centrally-located distal prong/peak 29, although this is less pronounced than for the first operative head 16.

Eight first channels 23 and eight second channels 28 alternate around a distal face of the discoidal body 27, each extending outwardly from the central prong/peak 29. A notch 25 is formed in the circumference of the discoidal body 27 at an outer end of each first channel 23, while the second channels 28 each extend outwardly beyond the notches 25 to the circumference of the discoidal body 27. This produces a petal-like effect, as shown best in FIG. 4C.

Each of the first and second channels 23, 28 focuses torsional-mode ultrasonic vibrations into material in contact with or closely adjacent to the distal face of the second operative head 26, as for the first operative head 16, with the same effects. In this case, however, when the second surgical tool 21 is used, the presence of the notches 25 eases flow of softened cement through to a proximal side of the second operative head 26.

The second surgical tool 11 is thus suitable for the same procedural steps as the first, piercing into the cement plug 5 that fills the medullary cavity, distally of the location 4 of the removed implant, to aid its removal.

Figure 5A:
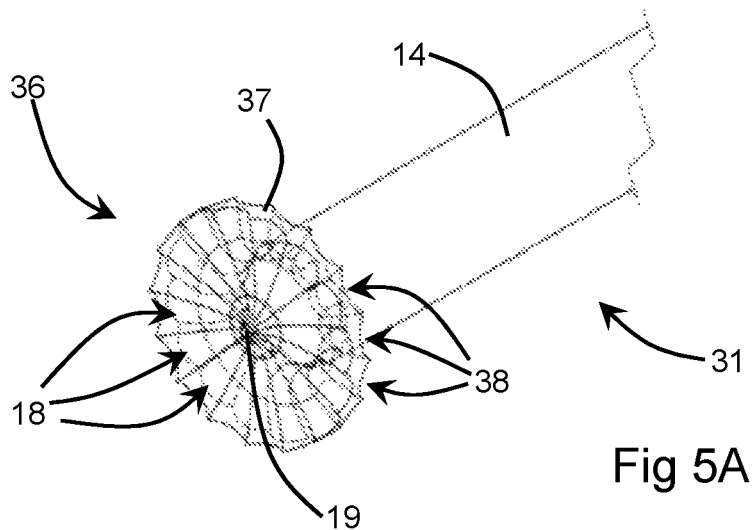
FIG. 5A is a scrap perspective view of an operative head of a third surgical tool embodying the present invention.
Figure 5B:
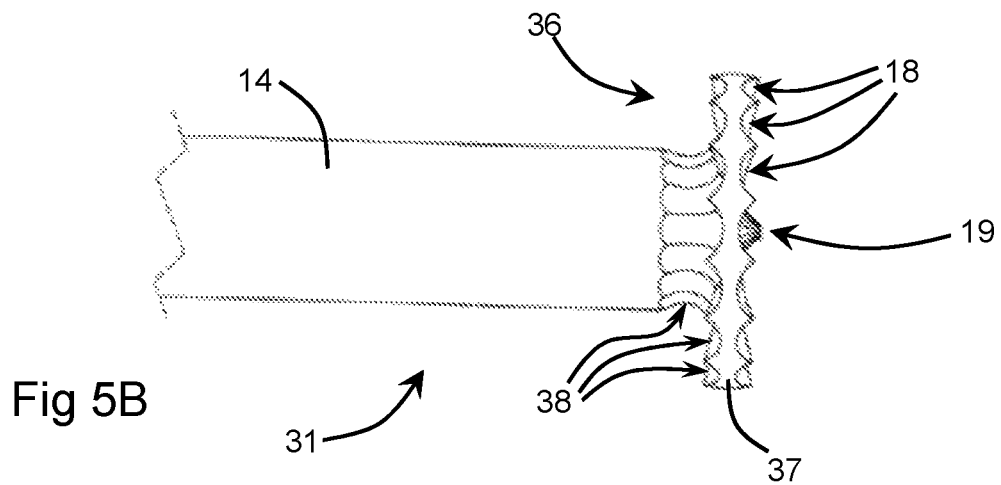
FIG. 5B is a scrap side elevation of the operative head of FIG. 5A.
Figure 5C:
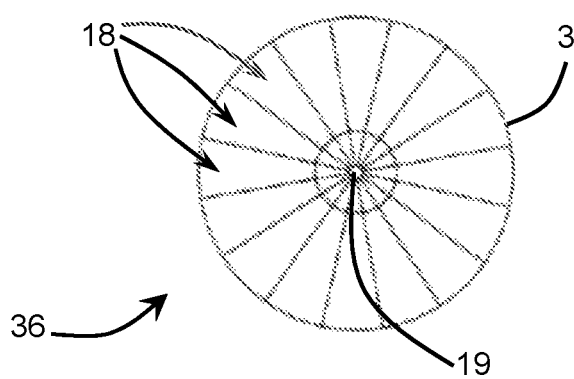
FIG. 5C is a distal end elevation of the operative head of FIG. 5A.

FIGS. 5A to 5C show a third operative head 36 of a third surgical tool 31. These are similar to the first surgical tool 11/operative head 16, with a discoidal body 37 similarly located on the distal end of the distal section 14 of the waveguide. There are sixteen round-bottomed channels 18 extending radially across the distal face of the discoidal body 37 from a centrally located peak/prong 19.

However, sixteen additional round-bottomed channels 38 radiate across a proximal face of the discoidal body 37, between its circumference and the waveguide, as well as a short distance longitudinally along the distal section 14 of the waveguide (shown in broken lines in FIG. 5A to distinguish the distal channels 18 from the proximal additional channels 38).

The third surgical tool 31 can thus be used in an identical manner to the first surgical tool 11 as described above, or it can be drawn (proximally) upwardly along walls of a hole in the cement plug 5 or along the layers 2 of cement lining the internal walls 3 of the bone 1 itself, softening cement, scooping it up and drawing it out of the bone cavity.

Figure 6A:
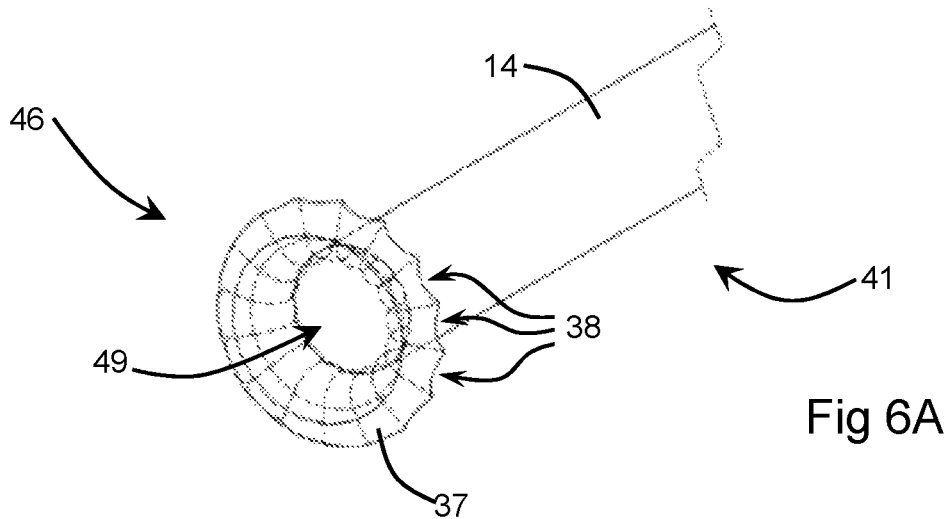
FIG. 6A is a scrap perspective view of an operative head of a fourth surgical tool embodying the present invention.
Figure 6B:
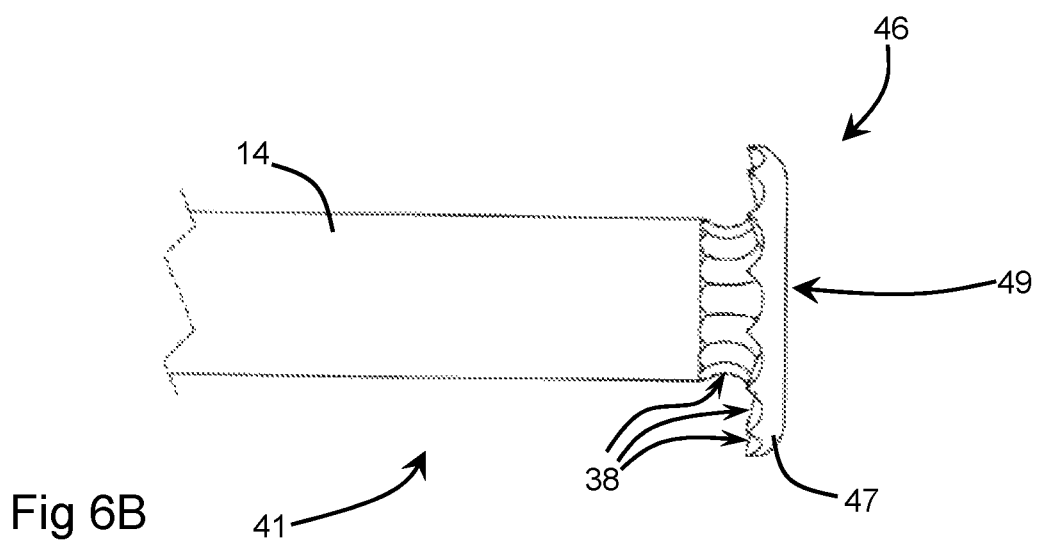
FIG. 6B is a scrap side elevation of the operative head of FIG. 6A.
Figure 6C:
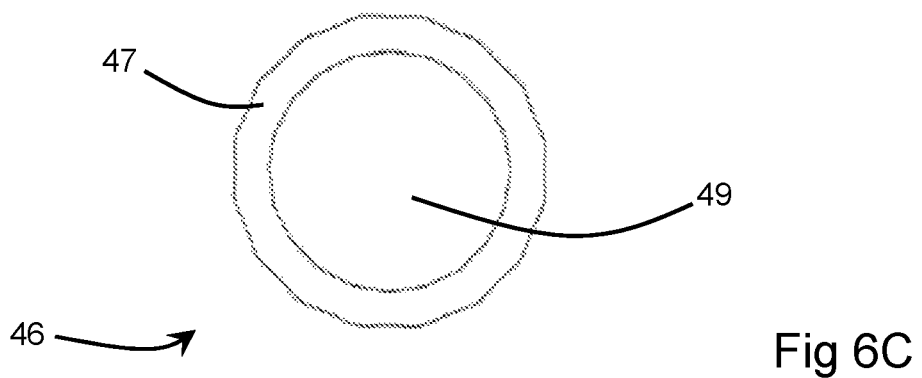
FIG. 6C is a distal end elevation of the operative head of FIG. 6B.
Figure 7A:
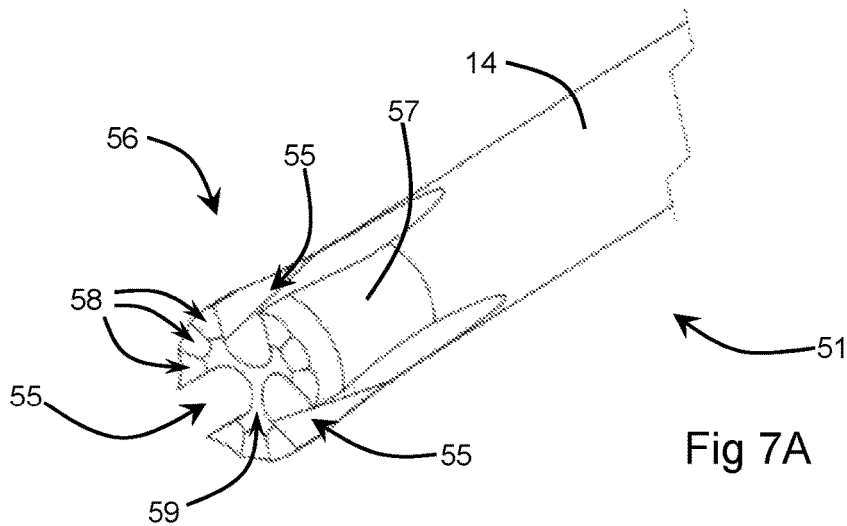
FIG. 7A is a scrap perspective view of an operative head of a fifth surgical tool embodying the present invention.
Figure 7B:
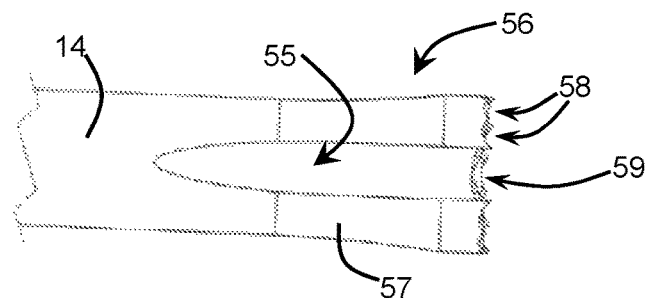
FIG. 7B is a scrap side elevation of the operative head of FIG. 7A.
Figure 7C:
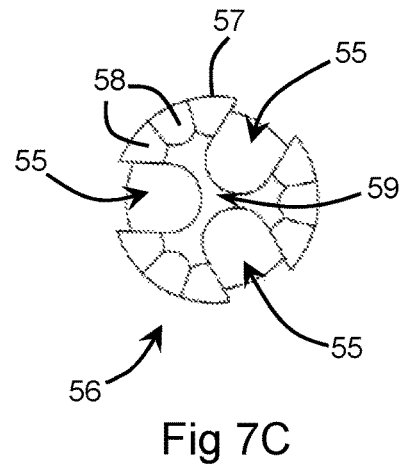
FIG. 7C is a distal end elevation of the operative head of FIG. 7A.
Figure 7D:
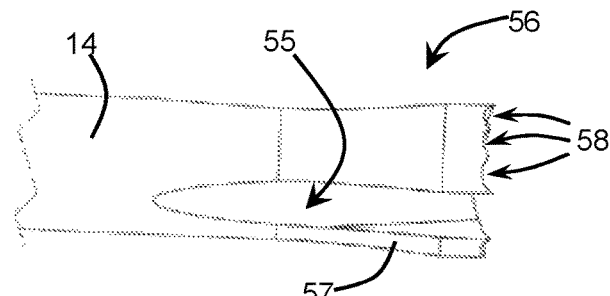
FIG. 7D is a scrap side elevation of the operative head of FIG. 7A, viewed at 90° to FIG. 7B.
Figure 7E:
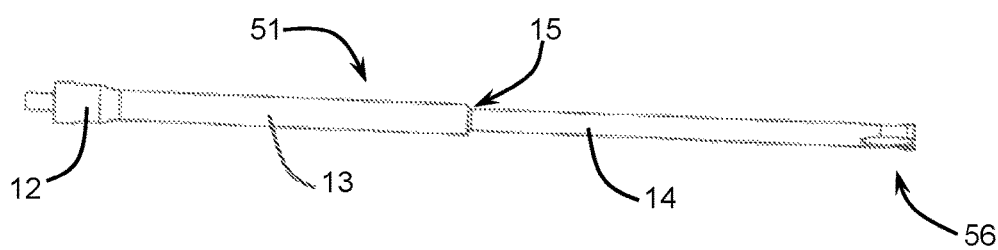
FIG. 7E is a side elevation of said fifth surgical tool.

FIGS. 6A to 6C show a fourth operative head 46 of a fourth surgical tool 41. This is similar to the third operative head 36/third surgical tool 31, described above, with a discoidal body 47 similarly located on the distal end of the distal section 14 of the waveguide. There are sixteen round-bottomed channels 38 radiating across the proximal face of the discoidal body 47, between its circumference and the waveguide, as well as a short distance longitudinally along the distal section 14 of the waveguide. (Again, shown in broken lines in FIG. 6A).

However, in the fourth operative head 46, the distal face 49 is featureless, and the circumference of the discoidal body 47 is bevelled distally.

The fourth surgical tool 41 is thus for use solely by being drawn (proximally) upwardly along cement forming walls of a previously formed hole, or along the layer 2 of cement lining the internal walls 3 of the bone 1, thus softening cement, scooping up the softened cement and drawing it out of the bone cavity.

FIGS. 7A to 7E show a fifth surgical tool 51 having a fifth operative head 56. This differs from the operative heads 16, 26, 36, 46 described above, as there is no outwardly extending discoidal body. Instead, a terminal portion 57 of the distal section 14 of the waveguide is formed so that it increases gradually and slightly in diameter towards a distal tip of the operative head 56. (In the example shown, the distal section 14 is five millimetres in diameter, and the terminal portion 57 is no more than six millimetres in diameter at its widest, at the distal tip).

A distal face of the distal tip comprises nine scalloped recesses 58 around its periphery and a larger scalloped recess 59 located centrally. The fifth operative head 56 is dissected into three branches or lobes by three radial slots 55. The radial slots 55 extend almost to a centre of the distal face, reducing the central larger scalloped recess 59 to a three-armed, generally Y shaped feature, each arm of which extends outwardly to meet a trio of the nine scalloped recesses 58. The radial slots 55 also extend proximally through the terminal portion 57, becoming gradually shallower as they go, ultimately tapering out a short distance along the distal section 14 of the waveguide.

The scalloped recesses 58, 59 each focus and project the energy of torsional-mode ultrasonic vibrations into materials in contact with or closely adjacent to the distal face. The periphal nine scalloped recesses 58 will have a greater effect, since the amplitude of the torsional-mode vibrations will be greater towards the circumference of the distal face (narrow though it may be).

The radial slots 55 serve to allow cement softened by the ultrasonic vibrations to pass through the fifth operative head 56 to its proximal side; they hence generally correspond in function to the notches 25 of the second operative head 26 above, allowing for the different geometries of the respective operative heads 26, 56.

The fifth surgical tool 51 is hence also of most use as a piercing tool to drive into bulk cement to form holes, for example when narrow holes are required, or to create "pilot holes" for subsequent broadening by one of the other surgical tools 11, 21, 31, 41 described above.

FIGS. 8A to 8E show a sixth surgical tool 61 with a sixth operative head 66, which differs significantly from a remainder of those shown herein. The sixth operative head 66 extends from the distal end of the distal section 14 of the waveguide, but unlike those described above, it has a generally fan-shaped form.

Figure 8A:
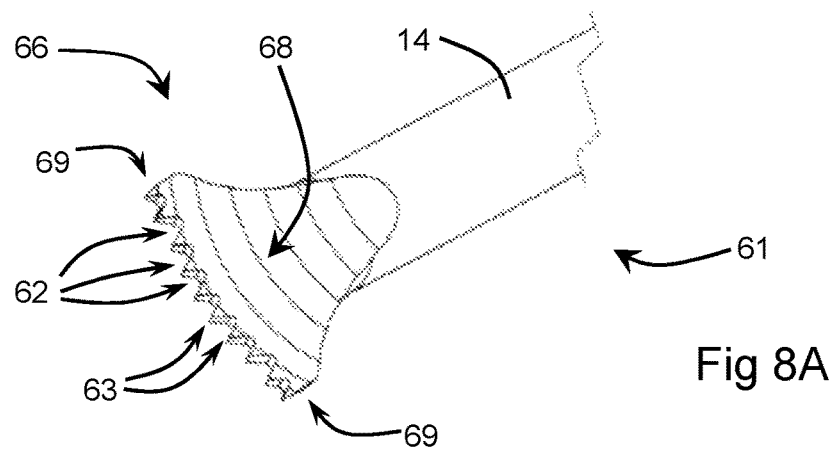
FIG. 8A is a scrap perspective view of an operative head of a sixth surgical tool embodying the present invention.
Figure 8B:
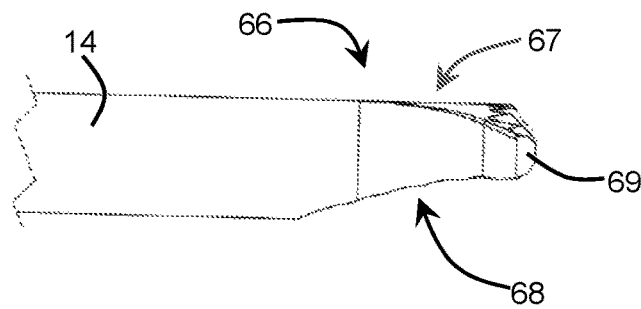
FIG. 8B is a scrap side elevation of the operative head of FIG. 8A.
Figure 8C:
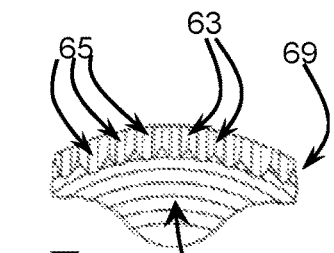
FIG. 8C is a distal end elevation of the operative head of FIG. 8A.
Figure 8D:
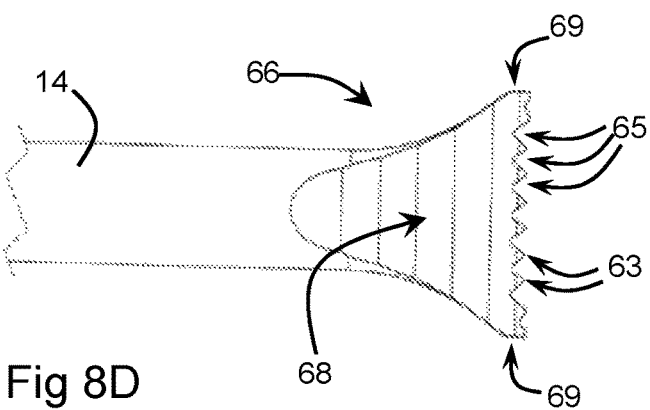
FIG. 8D is a scrap side elevation of the operative head of FIG. 8A, viewed at 90° to FIG. 8B.
Figure 8E:
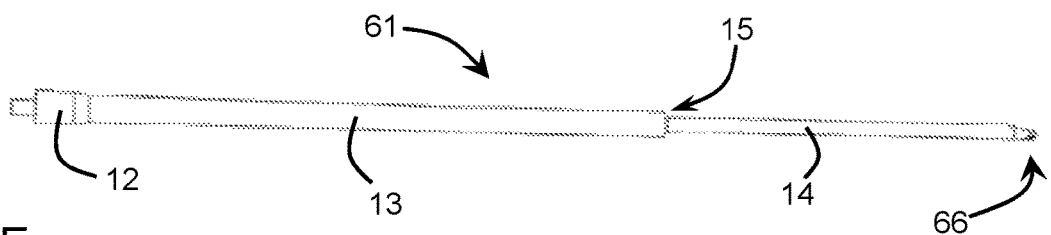
FIG. 8E is a side elevation of said sixth surgical tool.

The sixth operative head 66 fans out laterally as it extends to its distal edge 69, as shown in FIGS. 8A and 8D, but as shown in FIG. 8B, the sixth operative head 66 tapers in a wedge-shape when viewed from a direction at right angles to that of FIG. 8D. As shown in FIG. 8B, a first face 67 of the sixth operative head 66 extends substantially flush with an outer surface of the distal section 14 of the waveguide, but an opposite second face 68 is angled to extend distally towards the first face 67, producing the taper or wedge-profile. The second face 68 is slightly concave, as is best visible in FIGS. 8B and 8C.

As best shown in FIGS. 8A, 8C and 8D, the distal edge 69 of the sixth operative head 66 is provided with a series of small notches 65 along its length, defining between them a series of prongs or spikes 63.

Additionally, although the sixth operative head 66 has a substantially constant length, as measured to its (apparently straight) distal edge 69 (see FIG. 8D), the operative head 66 is profiled such that the distal edge 69 is curved when viewed from a direction parallel to the longitudinal axis of the waveguide (see FIG. 8C). The function of this shape is described below, but it should be noted that the curvature of the distal edge 69 is intended to be compatible with an internal curvature of the walls 3 of the femur 1.

As for the other operative heads described, the notches 65 and prongs 63 are not themselves intended as cutting/piercing features. Instead the notches 65 will serve to focus torsional-mode ultrasonic vibrations and project them immediately in front of the distal edge 69.

Figure 9A:
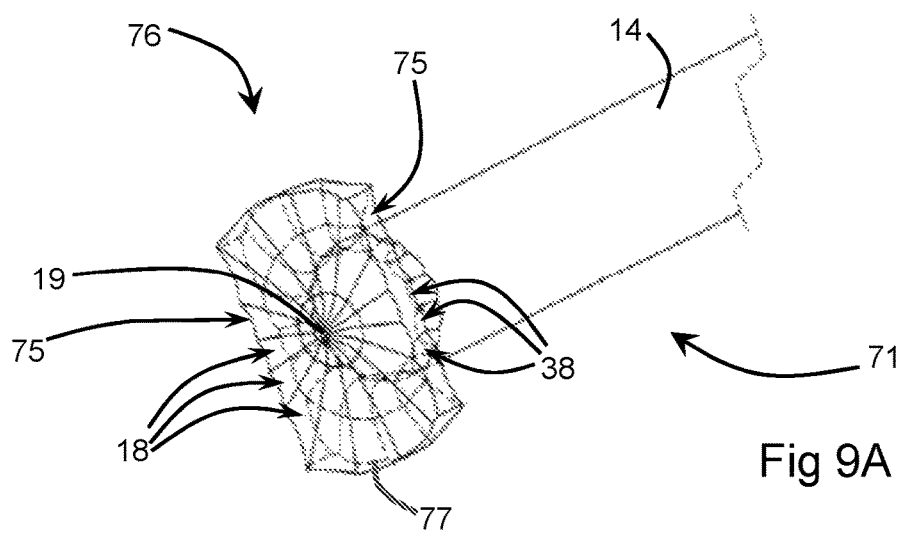
FIG. 9A is a scrap perspective view of an operative head of a seventh surgical tool embodying the present invention.
Figure 9B:
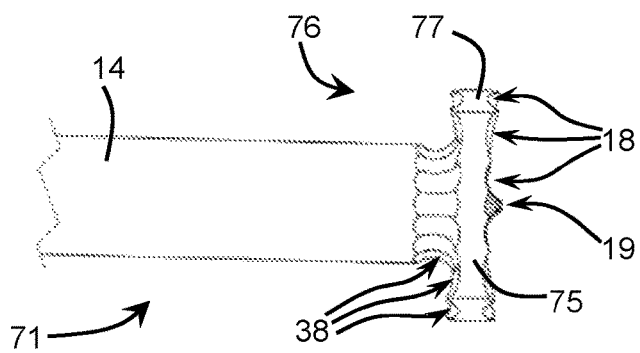
FIG. 9B is a scrap side elevation of the operative head of FIG. 9A.
Figure 9C:
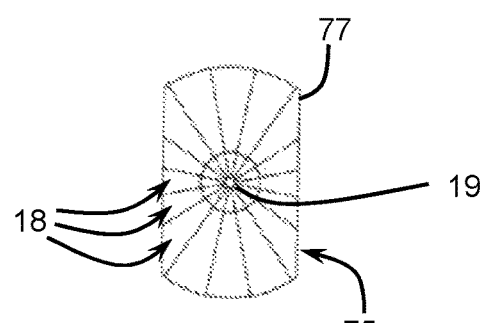
FIG. 9C is a distal end elevation of the operative head of FIG. 9A.
Figure 9D:
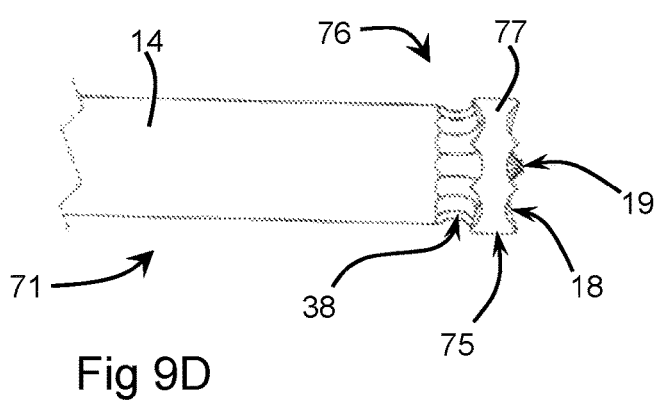
FIG. 9D is a scrap side elevation of the operative head of FIG. 9A, viewed at 90° to FIG. 9B.
Figure 10A:
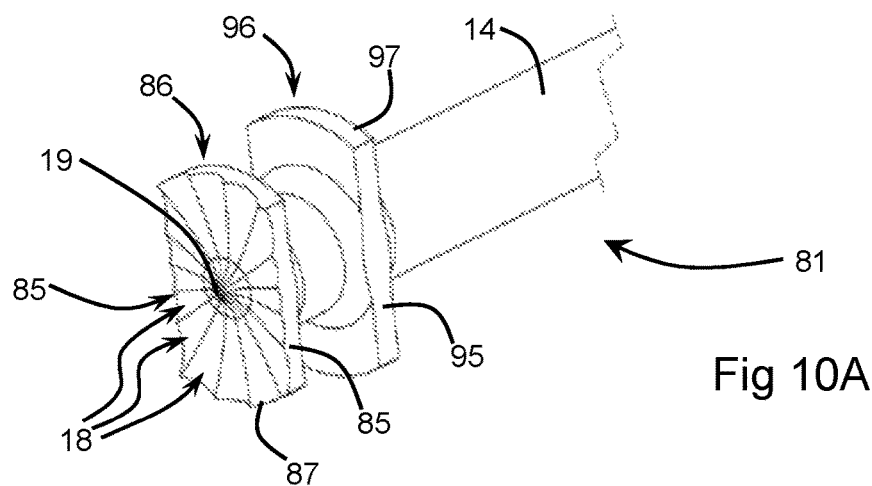
FIG. 10A is a scrap perspective view of an operative head of an eighth surgical tool embodying the present invention.
Figure 10B:
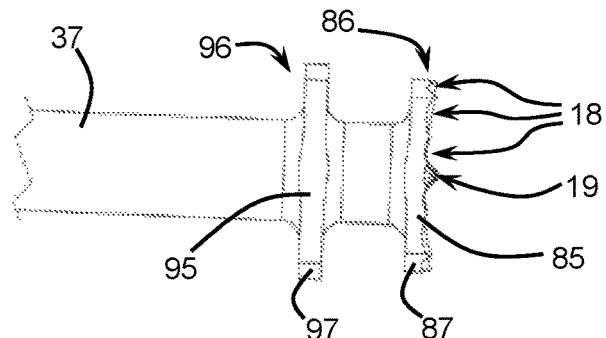
FIG. 10B is a scrap side elevation of the operative head of FIG. 10A.
Figure 10C:
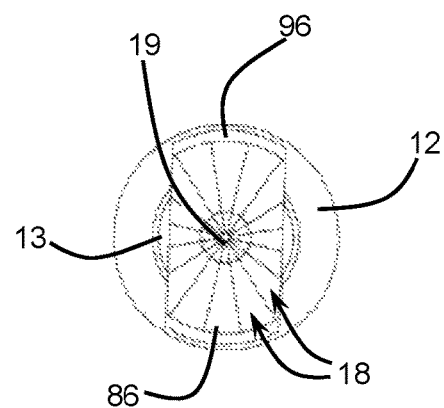
FIG. 10C is a distal end elevation of said eighth surgical tool.
Figure 10D:
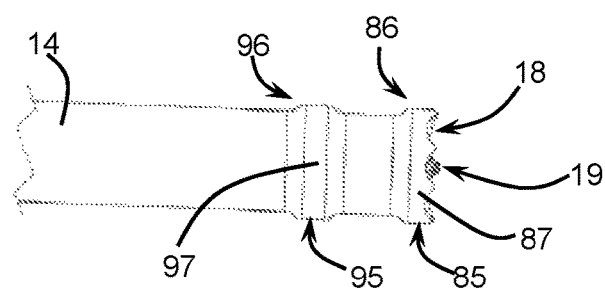
FIG. 10D is a scrap side elevation of the operative head of FIG. 10A, viewed at 90° to FIG. 10B.
Figure 10E:
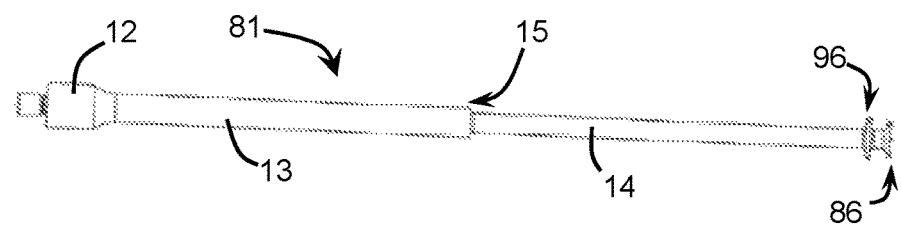
FIG. 10E is a side elevation of said eighth surgical tool embodying the present invention.

The sixth surgical tool 61 is often used in conjunction with the seventh surgical tool 71, of which the seventh operative head 76 is shown in FIGS. 9A to 9D. This operative head is related to that of the third surgical tool 31 (see FIGS. 4A to 4C). Rather than comprising a discoidal body, the seventh operative head 76 comprises a body 77 with two opposed straight sides and two opposed curved sides, as if the straight sides 75 had been formed by trimming segments off opposite sides of the third operative head 36. (see for example, FIG. 9D, illustrating how the operative head 76 is little broader that the distal section 24 of the waveguide). On the distal face, the round-bottomed channels 18 radiate outwardly from the prong or peak 19 to a periphery of the body 77, while on the proximal face, the additional channels 38 radiate between the waveguide and the periphery of the body 77, plus a short distance along the distal section of the waveguide.

Although the operative head 76 is no longer fully circularly symmetrical, it can still safely be activated by torsional-mode ultrasonic vibrations, with both the channels 18 on the distal face and the additional channels 38 on the proximal face being capable of focussing and projecting the vibrations into adjacent material.

Similar tools can be produced with the channels 18, 38 present only on the distal or proximal face of their operative head, respectively; these are not shown for conciseness.

The seventh and sixth surgical tools 71, 61 may be used together to remove the cement layer 2 lining the internal walls 3 of the bone 1. The seventh surgical tool 71 is used to create grooves extending radially into and through the cement layer 2 to the wall 3, by presenting the distal face of the (ultrasonically activated) operative head 71 to an upper end of the cement layer 2 and pushing distally to pierce the cement, or by presenting the proximal face to a lower region of the cement layer 2 and drawing proximally to scoop cement away. The widths of the grooves are governed by the separation between the two straight sides 75 of the operative head 76. These grooves are preferably created extending longitudinally of the cement layers 2, dividing the cement layer into a series of vertical strips.

Next, the distal edge 69 of the sixth surgical tool 61 is presented to the bone/cement interface at a proximal/upper end of the cement layer 2, and activated, projecting ultrasonic vibrations down between the wall 3 of the bone 1 and the cement layer 2. This separates the cement layer 2 from the wall 3, allowing the (wedge-shaped) operative head 66 of the tool 61 to be passed further and further down/distally of the interior of the bone 1 and peeling entire strips of cement off the walls 3 at once. This is a very efficient way of removing the cement layer 2 from the walls 3. (Thorough removal of this cement can be particularly important when the prosthetic site has become infected).

FIGS. 10A to 10E show an eighth surgical tool 81 which has an eighth operative head comprising a distal portion 86 and a proximal portion 96. The distal portion 86 is similar to the seventh operative head 76 (see FIGS. 9A to 9D), except for the absence of the additional channels 38 extending across its proximal face. The distal portion 86 thus comprises a body 87 having two curved edges and two parallel straight edges 85, with the channels 18 radiating across its distal face between the periphery and the central prong/peak 19. The proximal portion 96 of the eighth operative head also comprises a body 97 with two curved edges and two parallel straight edges 95, as if the straight sides 95 had been formed by trimming segments off opposing sides of a circular body. The proximal portion 96 is slightly larger than the distal portion 86 (see FIGS. 10B and 10C), and is aligned with it, but unlike the distal portion 86, the proximal portion 96 has no channels or recesses on either face.

The eighth surgical tool 81 is used to extract the distal cement plug 5 from the bone cavity, once the cement layers 2 have been removed from the walls 3. The tool 81 is ultrasonically activated and offered up to the plug 5, the channels 18 on the distal face of the distal portion 86 focussing the ultrasonic energy into the cement ahead of the tool 81, softening the cement. The tool 81 can thus be pushed down into the cement of the plug 5. The proximal portion 96 is sufficient, when activated, to keep adjacent cement softened, even in the absence of focussing channels or recesses. Once both portions 86, 96 of the eighth operative head are well within the cement of the plug 5, the tool 81 is twisted about its longitudinal axis through about a right angle. This drives the distal 86 and proximal portions 96 laterally into the softened cement, anchoring the tool 81 securely in the plug 5 when the ultrasonic vibrations are turned off and the cement hardens again. Application of an impact extractor hammer to the tool 81 can then break substantial portions or the whole of the cement plug 5 free from the bone cavity in a single procedural step, saving much time and effort compared to removing the cement of the plug 5 step by step using piercing and scraping tools.

A kit of tools containing some or all of the tools 11, 21, 31, 41, 51, 61, 71, 81 described above, operatively connected as required to a source of torsional-mode ultrasonic vibrations, can thus be used to remove intramedullary PMMA cement during revision of a joint prosthesis, more effectively and efficiently than previous systems.

An exemplary method would proceed as follows. After removing the implant from a femur, the procedure starts from a proximal end of the femur. The cylindrical shell of cement lining the walls of the medullary cavity is approached by dividing it longitudinally, using a groove-forming tool (such as the seventh tool 71 of FIGS. 9A to 9D). This instrument creates a slot in the cement shell, allowing the cement to be pulled/peeled away from the endosteal surface of the bone. Preferably, multiple slots are formed in this way, extending from a proximal end of the femur towards its distal end. Having segmented the cement shell, a fan-shaped tool (such as the sixth tool 61 of FIGS. 7A to 7E) can be inserted into the bone cement interface and used to separate entire segments of the cement shell from the bone.

Once these steps have been repeated sufficiently to remove the cement shell entirely and fully expose the distal cement plug, this can be removed either by repeated application of piercer and scraper tools or by embedding a tool such as the eighth tool 81 (shown in FIGS. 9A to 9E) into the plug, and using this to extract the plug. As for the piercer and scraper tools described, this tool has scalloped features on its distal face that generate high localised concentrations of torsional-mode ultrasonic energy, rapidly softening cement ahead of and adjacent the tool, allowing its head to be buried deep in the plug and rotated 90° into the mass of the cement. The cement can then be cooled by irrigation with saline, leaving the tool securely embedded; disconnection at its proximal end from the ultrasound source and connection of an implement such as a slap hammer can allow the plug to be broken free of the medullary cavity by inertial impact means. The alternative approach of removing the plug incrementally using piercer and scraper tools is likely to be less traumatic however, and so the surgeon has all the tools available, depending on his or her assessment of which approach will be best for the particular patient.

The invention claimed is:

1. A surgical tool for use in revision arthroplasty, adapted to be activated by torsional-mode ultrasonic vibrations, comprising an elongate waveguide adapted to transmit said ultrasonic vibrations to an operative head mounted adjacent a distal end of the elongate waveguide, wherein said operative head comprises a discoidal body extending transversely to a longitudinal axis of the elongate waveguide and having a distal face and a proximal face, and said discoidal body comprises a plurality of elongate channels extending across said distal face, each of said elongate channels being adapted to focus and project torsional-mode ultrasonic vibrations into bone cement and other materials in contact with said distal face.

2. The surgical tool as claimed in claim 1, wherein said discoidal body extends orthogonally to the longitudinal axis of the elongate waveguide.

3. The surgical tool as claimed in claim 1, wherein said discoidal body extends outwardly to all sides from the elongate waveguide.

4. The surgical tool as claimed in claim 1, wherein said discoidal body comprises also comprises a plurality of elongate channels extending across said proximal face, each said plurality of elongate channels extending across said proximal face being adapted to focus and project torsional-mode ultrasonic vibrations into bone cement and other materials in contact with said proximal face.

5. The surgical tool as claimed in claim 4, wherein said plurality of elongate channels extending across said proximal face of said discoidal body radiate outwardly from a junction of said discoidal body with the elongate waveguide towards a circumference of said discoidal body.

6. The surgical tool as claimed in claim 5, wherein each of the plurality of elongate channels extending across the proximal face of said discoidal body extend to the circumference of the discoidal body.

7. The surgical tool as claimed in claim 4, wherein each of said plurality of elongate channels extending across the proximal face of the discoidal body comprises a round-bottomed channel.

8. The surgical tool of claim 4, wherein a bottom of each of the plurality of elongate channels extending across the distal face of said discoidal body and a bottom of each of the plurality of elongate channels extending across the proximal face of said discoidal body focus and project torsional-mode ultrasonic vibrations into bone cement and other materials in contact with a corresponding face of said discoidal body.

9. The surgical tool as claimed in claim 1, wherein said discoidal body is substantially circular.

10. The surgical tool as claimed in claim 1, wherein said discoidal body comprises a plurality of shallow notches or recesses arranged around its circumference.

11. The surgical tool as claimed in claim 1, wherein each of said plurality of elongate channels extending across the distal face of the discoidal body comprises a round-bottomed channel.

12. The surgical tool as claimed in claim 1, wherein the distal face and the proximal face of the discoidal body are each generally planar.

13. A surgical tool for use in revision arthroplasty, adapted to be activated by torsional-mode ultrasonic vibrations, comprising an elongate waveguide adapted to transmit said ultrasonic vibrations to an operative head mounted adjacent a distal end of the elongate waveguide, wherein said operative head comprises a discoidal body extending transversely to a longitudinal axis of the elongate waveguide and having a distal face and a proximal face, and said discoidal body comprises a plurality of elongate channels extending across said proximal face, each of said plurality of elongate channels extending across said proximal face being adapted to focus and project torsional-mode ultrasonic vibrations into bone cement and other materials in contact with said proximal face.

14. The surgical tool as claimed in claim 13, wherein said discoidal body extends orthogonally to the longitudinal axis of the elongate waveguide.

15. The surgical tool as claimed in claim 13, wherein said plurality of elongate channels extending across said proximal face radiate outwardly across said proximal face from a junction of said discoidal body with the elongate waveguide towards a circumference of said discoidal body.

16. The surgical tool as claimed in claim 15, wherein each of the plurality of elongate channels extending across the proximal face of said discoidal body extend to the circumference of the discoidal body.

17. The surgical tool as claimed in claim 13, wherein each of said plurality of elongate channels extending across the proximal face of the discoidal body comprises a round-bottomed channel.

18. The surgical tool as claimed in claim 13, wherein the discoidal body extends outwardly to all sides from the elongate waveguide.

19. The surgical tool as claimed in claim 13, wherein the discoidal body is substantially circular.

20. The surgical tool as claimed in claim 13, wherein the distal face and the proximal face of the discoidal body are each generally planar.

* * * * *